(12) United States Patent
Moles

(10) Patent No.: US 6,770,322 B1
(45) Date of Patent: Aug. 3, 2004

(54) METHOD OF MAKING A PLATFORM FOR USE IN A SENSOR IN A MICROFLUIDIC DEVICE

(75) Inventor: Donald R. Moles, Cedarville, OH (US)

(73) Assignee: YSI Incorporated, Yellow Springs, CO (US)

( * ) Notice: Subject to any disclaimer, the term of this patent is extended or adjusted under 35 U.S.C. 154(b) by 3 days.

(21) Appl. No.: 09/799,820

(22) Filed: Mar. 2, 2001

Related U.S. Application Data

(60) Provisional application No. 60/186,930, filed on Mar. 3, 2000.

(51) Int. Cl.$^7$ .............................. B05D 7/22; B05D 1/36
(52) U.S. Cl. ........................ 427/230; 427/404; 427/409
(58) Field of Search .............................. 427/58, 96, 97, 427/123, 404, 409, 2.1, 2.11, 2.3, 230, 237, 307; 204/403.01, 403.06; 435/287.2

(56) References Cited

U.S. PATENT DOCUMENTS

| | | | |
|---|---|---|---|
| 2,510,262 A | 6/1950 | Sollner et al. | 264/232 |
| 3,539,455 A | 11/1970 | Clark, Jr. | 205/778 |
| 3,668,101 A | 6/1972 | Bergman | 204/415 |
| 4,073,713 A | 2/1978 | Newman | 204/403.9 |
| 4,454,007 A | 6/1984 | Pace | 205/778 |
| 4,680,268 A | 7/1987 | Clark, Jr. | 205/778 |
| 4,721,677 A | 1/1988 | Clark, Jr. | 600/316 |
| 4,858,883 A | 8/1989 | Webster | 251/61.1 |
| 4,874,500 A * | 10/1989 | Madou et al. | 204/412 |
| 4,889,611 A | 12/1989 | Blough, Jr. | 204/411 |
| 4,897,153 A * | 1/1990 | Cole et al. | 216/18 |
| 5,063,081 A | 11/1991 | Cozzette et al. | 435/4 |
| 5,120,504 A | 6/1992 | Petro-Roy et al. | 422/58 |
| 5,194,133 A | 3/1993 | Clark et al. | 204/608 |
| 5,238,548 A | 8/1993 | van der Wal et al. | 204/418 |
| 5,350,518 A | 9/1994 | Hiti et al. | 210/638 |
| 5,393,401 A | 2/1995 | Knoll | 204/403.06 |
| 5,443,890 A | 8/1995 | Ohman | 428/167 |
| 5,468,374 A | 11/1995 | Knoll | 210/96.2 |
| 5,631,447 A * | 5/1997 | Smith et al. | 174/260 |
| 5,660,728 A | 8/1997 | Saaski et al. | 210/251 |
| 5,846,392 A | 12/1998 | Knoll | 205/778 |
| 5,882,494 A | 3/1999 | Van Antwerp | 600/347 |
| 5,932,799 A | 8/1999 | Moles | 73/53.01 |
| 6,071,597 A * | 6/2000 | Yang et al. | 428/209 |
| 6,073,482 A | 6/2000 | Moles | 73/53.01 |

FOREIGN PATENT DOCUMENTS

| | | |
|---|---|---|
| EP | 0 750 744 B1 | 10/1995 |
| WO | WO 95/08716 | 3/1995 |
| WO | WO 99/03584 A1 * | 1/1999 ............. B01L/3/00 |

OTHER PUBLICATIONS

S. Sampath and O. Lev, "Inert Metal–Modified, Composite Ceramic–Carbon, Amperometric Biosensors: Renewable, Controlled Reactive Layer", 7/96, *Analytical Chemistry*, vol. 68, No 13.

J. Perdomo et al., "Containment sensors for the determination of L–lactate and glucose", 8/98, *Biosensors & Bioelectronics*.

D. Thevenot, "Problems in Adapting a Glucose–Oxidase Electrochemical Sensor into an Implantable Glucose–Sensing Device", May–Jun. 1982, *Diabetes Care*, vol. 5 No. 3.

R. Steinkuhl et al., "Glucose Sensor in Containment Technology", 1994, *Horm. Metab. Res. 26*.

\* cited by examiner

*Primary Examiner*—Shrive P. Beck
*Assistant Examiner*—William Phillip Fletcher, III
(74) *Attorney, Agent, or Firm*—Thompson Hine LLP

(57) ABSTRACT

A method is provided for constructing a platform for use in a sensor in a microfluidic device. The method may include the steps of selecting a polymeric film, laser drilling at least one frustoconical pore in the film, depositing a layer of metal suitable for use as an electrode over a wall of the pore, and depositing a membrane capable of detecting an analyte in the pore over the metal layer. The method may also include the additional step of forming a diffusion limiting layer in the pore at an exit end of the pore before depositing the membrane capable of detecting an analyte.

10 Claims, 4 Drawing Sheets

US 6,770,322 B1

METHOD OF MAKING A PLATFORM FOR USE IN A SENSOR IN A MICROFLUIDIC DEVICE

CROSS REFERENCE TO RELATED APPLICATIONS

This application claims priority from U.S. Provisional Patent Application Serial No. 60/186,930 filed Mar. 3, 2000.

BACKGROUND OF THE INVENTION

The invention relates generally to microfluidic devices, and more specifically to the pores constructed in platforms for use in microfluidic sensors, the shape and structure of such pores, methods for creating such pores, and sensors made from platforms including such pores.

In the fabrication of microfluidic devices, it is sometimes desired to create pores in the platforms used in the microfluidic devices. U.S. Pat. No. 5,846,392 to Knoll, the contents of which are herein incorporated by reference, discloses the fabrication of miniaturized circulatory measuring chambers in a carrier platform in which the chambers taper from a wide opening at one surface to a narrower opening at the opposite surface of the carrier platform. The carrier platform disclosed in the Knoll patent is made from silicon and the chamber is etched into the silicon using anisotropic or isotropic etching processes. The wide opening of the chambers are sealed with a glass plate and the narrower openings open on a channel through which an analyte is conducted to the chambers. The techniques described in the Knoll patent form chambers that have a frustopyrimidal shape. However, the methods and materials described in the Knoll patent may not be well adapted for use in the manufacture of microfluidic devices in material platforms other than silicon.

SUMMARY OF THE INVENTION

The present invention provides a microfluidic device having a sensor platform that is formed by perforating a film, such as a plastic film of an aromatic polyimide. A film prepared in this manner (platform) can then be assembled into a sensor for use in a microfluidic device using any of the film bonding techniques which are well known in the art including heat sealing, application of adhesives or clamping. Sensors constructed in accordance with the platforms of the present invention may be capable of providing improved responsiveness, sensitivity and, in particular, improved linearity over prior art sensors used in microfluidic devices. Examples of microfluidic devices of the type in which the platforms described herein would be useful are described in U.S. Pat. Nos. 5,932,799 and 6,073,482 assigned to YSI Incorporated, and the references cited therein. As noted in those patents, the pores in the platforms may be connected by fluid flow channels to create microfluidic sensors in accordance with the present invention.

In one embodiment of the invention, frustoconical pores may be perforated in the film for use in a sensor platform by laser drilling techniques. Laser drilling of films, and plastic films in particular, generally yields pores having minimal taper angles, generally less than about 15 degrees (measured with respect to vertical). Films considered operable in connection with the present invention include polyimide films and polyester films including MYLAR™. Specifically, self-bonding polyimide as described in U.S. Pat. No. 5,932,799 assigned to YSI, the contents of which are herein incorporated by reference, is considered operable in connection with the present invention. Of course, other films may be used and are considered within the scope of the present invention. Additionally, platforms and sensors incorporating such platforms in accordance with the present invention may be incorporated in microfluidic devices constructed from self-bondable polyimide films in accordance with the teachings of the '799 patent.

One factor limiting film selection for use in sensor platforms is the ability to deposit an electrical contact on the sides of the pores utilized in such platforms. For application of platinum electrodes to polyimide, it has been found particularly effective in one embodiment to first deposit a layer of diamond-like carbon amorphous film which functions as an oxygen and moisture barrier to protect the adhesion layer which is generally formed next. This barrier layer may typically be about 200 to 800 Angstroms thick. The adhesion layer is generally a layer or a metal such as chromium or titanium and typically may be about 200 to 400 Angstroms thick. The platinum electrode may typically be about 1000 to 2000 Angstroms or greater thick.

In some embodiments of the invention, sensors produced using the perforated film platforms disclosed herein utilizing a diffusion limiting film exhibit essentially linear responses for analyte concentrations of up to about 60 millimolar (mM). In other embodiments, sensors produced using the perforated films disclosed herein exhibit essentially linear responses for analyte concentrations up to about 50 mM without the need for a diffusion limiting film. It is believed that one factor contributing to the improved linearity in the sensor responses exhibited by these embodiments is the frustoconical pore geometry, as opposed to the frustopyrimidal pore geometry disclosed in the Knoll patent. It will be apparent to one of ordinary skill in the art upon review of the description that many of the embodiments disclosed herein may be combined or modified without departing from the scope of the invention.

DETAILED DESCRIPTION

Figure 1:
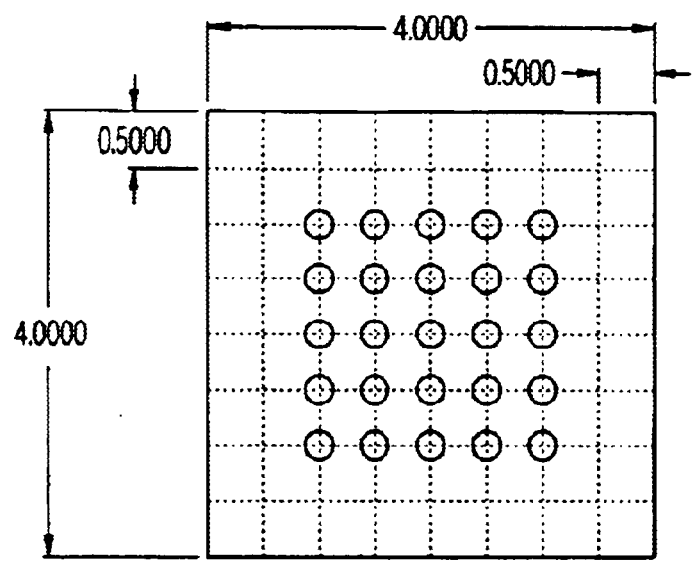
FIG. 1 is a schematic diagram of the arrangement of wafer platforms on a sheet of film in accordance with an embodiment of the invention.
Figure 2:
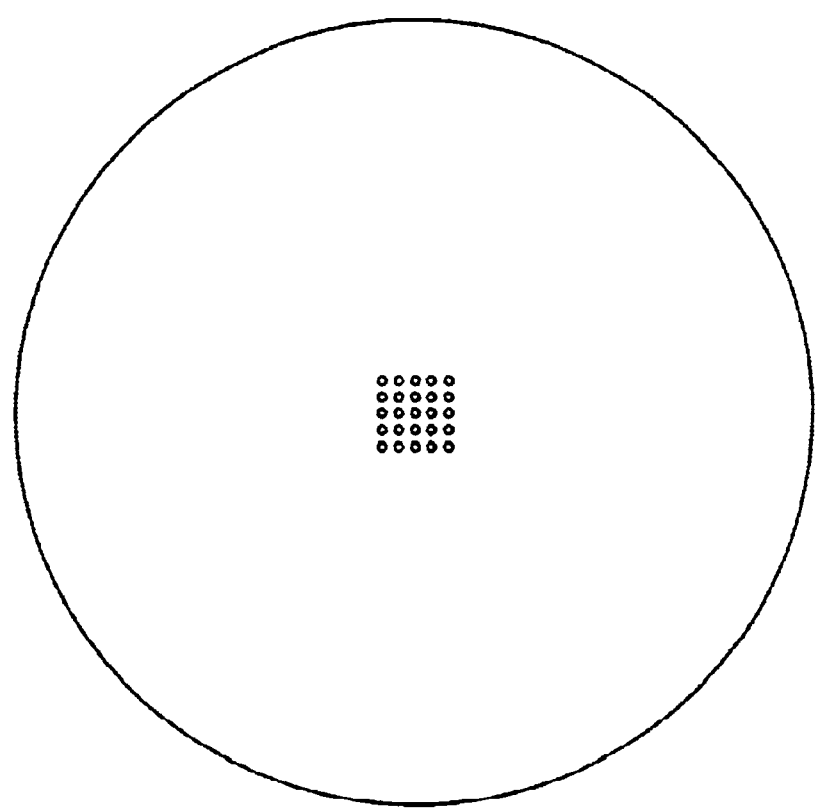
FIG. 2 is a magnified view of a wafer platform having pores drilled therein in accordance with an embodiment of the invention.

In accordance with the invention, polymeric film of any suitable thickness may be used to produce platform wafers useful in the production of sensors for use in microfluidic devices. It has been found that DuPont KAPTON™ VN film in 2 and 5 mil thicknesses would be operable in an embodiment of the invention. As shown best in FIG. 1, in an embodiment of the invention, wafers may be arranged on a sheet of film in a 5×5 pattern with the center of each wafer being spaced one-half inch apart thereby creating 25 wafers on each sheet of film. The term "wafer" as used herein refers to a device having one or a plurality of different sensors. As shown best in FIG. 2, in an embodiment of the invention, each wafer may be laser-drilled in 5×5 square arrays to create 25 frustoconically shaped pores. As shown best in FIG. 3, the pore diameter drilled by the laser may be varied between separate wafers to create pores having different geometries.

In an embodiment of the invention, the pores may be drilled through the chosen film material by UV photochemical ablation utilizing an excimer laser source operating at a suitable emission wavelength. Wavelengths that are considered operable in accordance with the invention include wavelengths of 193, 248, or 308 nm, among others. The output beam of the laser may be directed through a suitable mask that may be a metal stencil or a patterned film coating on a transparent substrate or other mask as is known in the art. The mask may include one or more apertures defining the pore or pore pattern to be drilled. The portion of the beam transmitted through the mask may then be imaged upon, and, appropriately aligned to, the target film at an optical demagnification ratio sufficient to achieve suitable energy density on the target film to effect the desired photochemical ablation process. A sufficient number of laser pulses at this energy density may then be applied to the target film to carry the photochemical ablation process through the full thickness of the target film. Upon completion of laser ablation through the film using the desired mask, the mask can then be repositioned with respect to the target film upon another wafer to drill additional pores or pore patterns in a similar fashion as desired.

Figure 3:
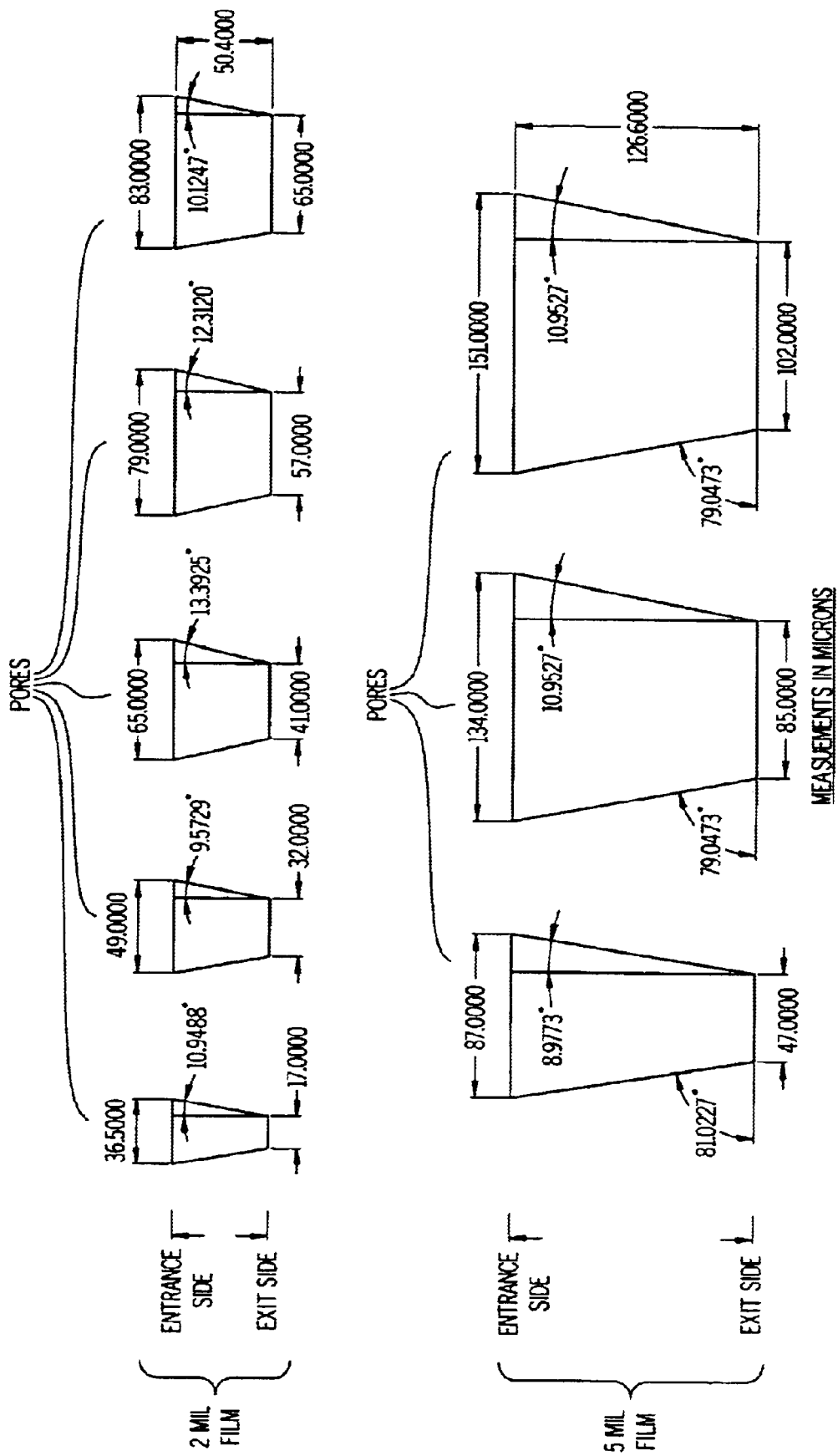
FIG. 3 is a cutaway side elevational view of individual frustoconical pores drilled in film wafer platforms in accordance with an embodiment of the invention.

In an embodiment of the invention wherein the laser drilling technique is used to drill through the entire thickness of the film, each pore consists of an entrance side and an exit side to the pore. In this embodiment, as best seen in FIG. 3, the entrance side of the pore is generally slightly larger in diameter than the diameter of the exit side of the pore, thereby making the pore generally frutsoconical in shape.

Upon completion of the laser drilling of the film, the wafers may be cleaned in order to remove residue created by the laser ablation process using a suitable material or solvent. Operable cleaning materials would include TEX-WIPE™ iso-propyl alchohol (IPA) cloths. To further clean the drilled wafers, the wafers may be then subjected to an oxygen plasma etching as is known in the art. It is noted that oxygen plasma etching may slightly increase the size and shape of the drilled pores.

In one embodiment of the invention, electrodes may be formed in the pores by initially coating the wafers with a layer of diamond-like carbon amorphous film. This can be accomplished by any method known in the art including chemical vapor deposition (CVD). The wafers can then be sputtered with a metal, such as chromium and/or platinum so that the interior surfaces of the pores are coated. In this way, the pores are enabled to act as electrodes in a corresponding electrochemical reaction when the wafers are used as platforms in sensors used in microfluidic devices. Next, in an embodiment of the invention, the wafers may be mounted to a sheet of film, such as MYLAR™ to stiffen the wafers and provide a recess to keep the pore face from contacting the surface on which it may be laying. The MYLAR™ may be applied to the wafer film using a double sided tape and the MYLAR™ may be applied to the "exit" side of the wafer. After the MYLAR™ is applied to the drilled film, the wafer platforms may be punched out of the film.

In an embodiment of the invention, the wafer platforms may be further processed into sensors as follows. In embodiments of the invention wherein a diffusion limiting layer may be desired, the metallically treated pores may first be filled with a suitable diffusion polymer solution, which, after drying, and as will be discussed in detail below, creates a film that serves as a diffusion barrier. Then the remaining pore volume may be filled with the desired membrane enzyme mixture. Next, after curing the enzyme solution, a wire may be attached to the electrode outside the region of the pores. The cured enzyme and the entire backside of the sensor may then be covered with a protective film of silicone rubber to prevent the enzyme solution from flowing through the pore and contaminating the backside of any microfluidic device into which the sensor is incorporated.

In the embodiments wherein a diffusion-controlling outer membrane is incorporated into the sensor, those membranes may be made of polyvinyl alcohol (PVA) by filling the pores with a PVA solution (which may be a 5% solution of 100% hydrolyzed PVA having an average molecular weight of 86,000). The excess PVA may then be wiped from the surface of the sensor, thereby allowing approximately one pore volume of solution to remain in the pore to evaporate. During evaporation the remaining solution is drawn to exit end of the pore due to capillary forces. This action thus creates a diffusion barrier at the exit end of the pore. After drying, the film made thereby can be cured in a manner known in the art so as to cross-link the PVA making it less apt to re-dissolve when exposed to solvents, etc.

In embodiments wherein a diffusion-controlling outer membrane is not incorporated, the enzyme solution may be applied in a similar fashion as with the PVA except that the excess solution may be applied so that a thicker membrane of chemically cured enzyme material remains in the pore. A suitable enzyme solution for use in the pores to create the sensors may include glucose oxidase (12.5 mg) in a solution (125 $\mu$l) of buffer salts (citrate-succinate buffer, pH 5.5). Glutaraldehyde (187.5 $\mu$l of 2.5% solution) may then be added to this mixture to induce chemical cross-linking of the oxidase protein.

Figure 4:
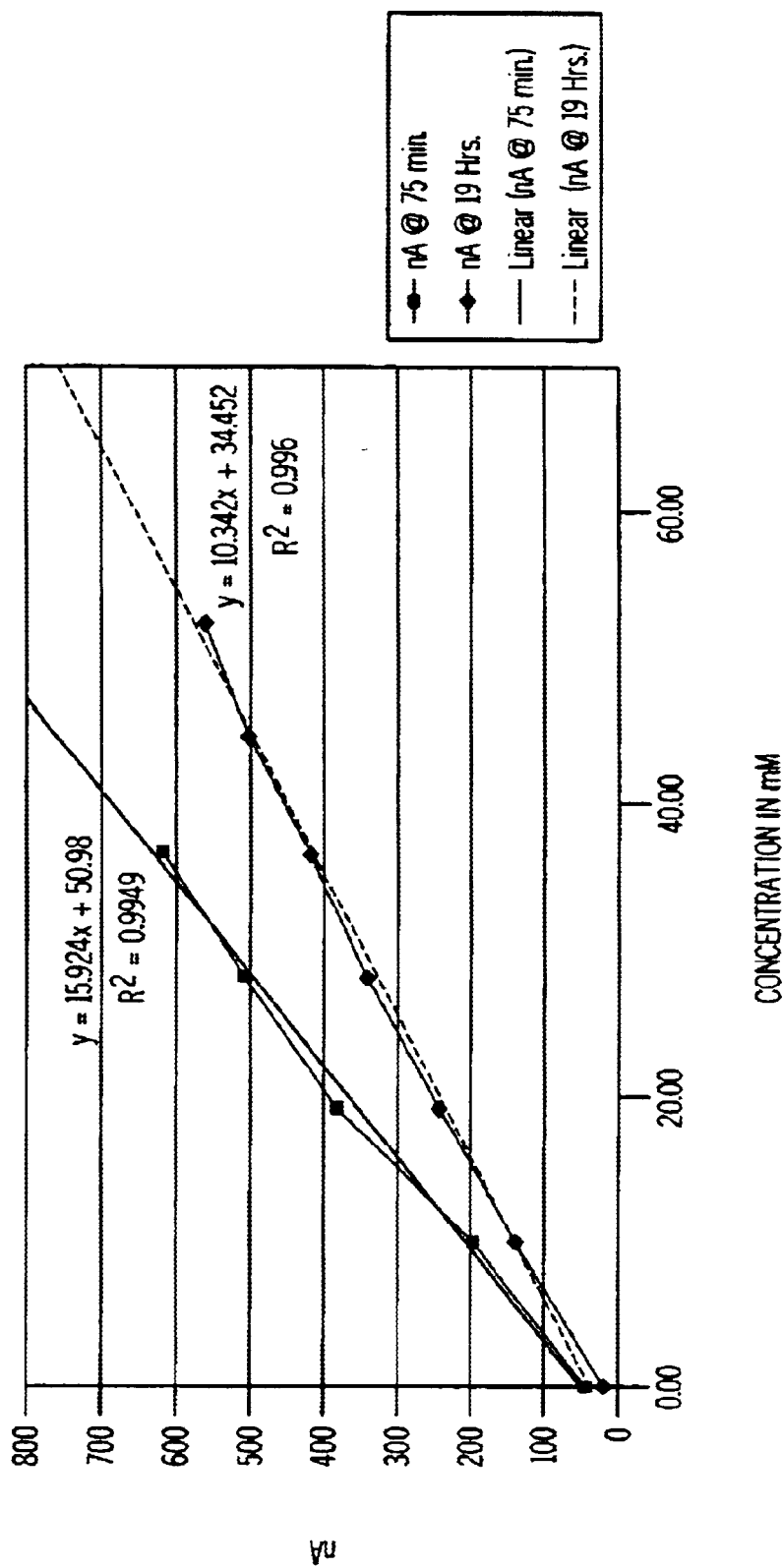
FIG. 4 is a graph of current vs. Dex concentration for a sensor incorporating a wafer platform including a diffusion layer in accordance with an embodiment of the invention.
Figure 5:
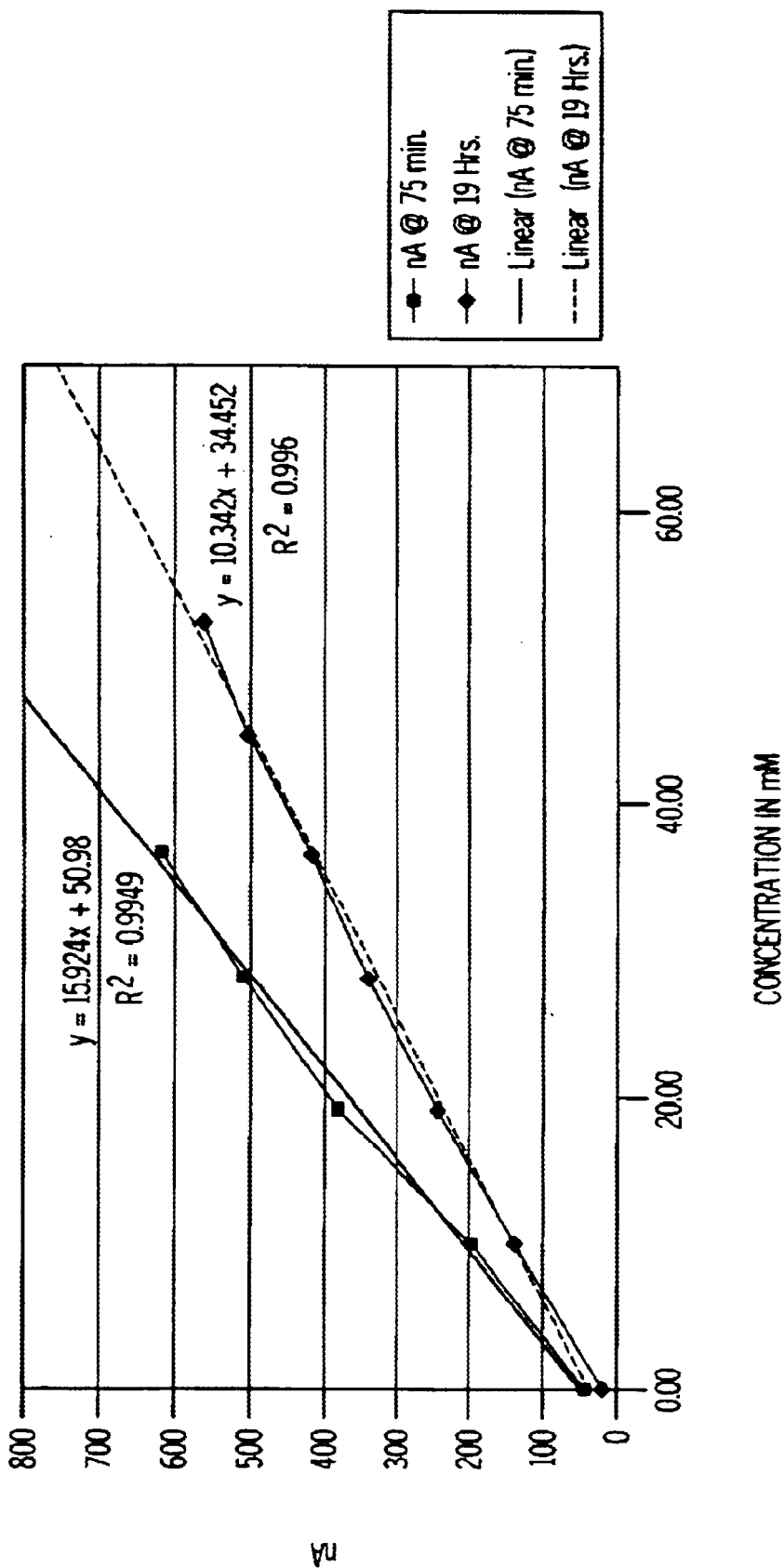
FIG. 5 is a graph of current vs. Dex concentration for a sensor incorporating a wafer platform not including a diffusion layer in accordance with an embodiment of the invention.

A As best shown in FIGS. 4 and 5, sensors created using wafer platforms in accordance with the invention exhibit relatively good linearity with good sensitivity. Specifically, FIG. 4 shows the current vs. Dextrose ("Dex") concentration using a sensor made in accordance with the invention incorporating a diffusion membrane as discussed herein and FIG. 5 shows the current vs. Dex concentration using a sensor made in accordance with the invention not incorporating a diffusion membrane.

EXAMPLES

Eight 4"×4" sheets of DuPont KAPTON™ VN were prepared, three of 500 (5 mil) VN and five of 200 (2 mil) VN. The wafer platforms were arranged on each sheet in a 5×5 pattern with the center of each wafer being spaced one-half inch apart thereby creating 25 wafers on each sheet of KAPTON™ film. Each wafer then was laser-drilled in 5×5 square arrays to create 25 frustoconically shaped pores in each wafer by UV photochemical ablation, utilizing an excimer laser source operating at an emission wavelength of 193, 248, or 308 nm. The pores drilled into the 2 mil KAPTON™ were spaced 5 mils apart pores (measured from the center of each respective pore) and the pores on the 5 mil KAPTON™ were spaced 10 mils apart. The pore diameter was maintained at a constant single nominal pore size for pores drilled in each respective wafer but was varied between separate wafers.

The pores were drilled through the target KAPTON™ film by aiming the output beam of the laser through a mask, typically a metal stencil or a patterned film coating on a transparent substrate, consisting of one or more apertures defining the hole or hole pattern to be drilled. The portion of the beam transmitted through the mask was imaged upon, and appropriately aligned to the target material, at an optical demagnification ratio sufficient to achieve suitable energy density on the target material to effect the desired photochemical ablation process. A sufficient number of laser pulses at this energy density were then applied to the target material to carry the photochemical ablation process through the full thickness of the target material. The projected mask image was then repositioned with respect to the target material to drill additional holes (or hole patterns) in a similar fashion.

After drilling, each pore consisted of an entrance side and an exit side to the pore. The entrance sides of the pores were slightly larger than the exit sides, thereby making the pore frustoconical in shape. The actual pore dimensions are shown in the table below as they were measured with an inverted microscope, where H is height of the frustum, R1 is the radius of the larger (entrance) opening, and R2 is the radius of the smaller (exit) opening. Please note that the table of areas and volumes of the various sizes of conically shaped pores are each modeled as a frustum of a cone.

Pore Diameters Before Plasma Cleaning

|       | Material Code | Exit Dia. $\mu$ | Entrance Dia $\mu$ | Comments |
|-------|---------------|-----------------|--------------------|----------|
| Wafer #1: | 200VN | 17 | 36.5 | very elliptical |
| #2: | 200VN | 32 | 49 | |
| #3: | 200VN | 41 | 65 | |
| #4: | 200VN | 57 | 79 | |
| #5: | 200VN | 65 | 83 | less elliptical |
| #6: | 500VN | 47 | 87 | |
| #7: | 500VN | 85 | 134 | |
| #8: | 500VN | 102 | 151 | |

The following measurements were taken after two cycles in the plasma-etcher. Settings were: 5 minutes, RF power=150 W, flow rate=150 m/min.

| In mils | | | | | In microns | | | | |
|---|---|---|---|---|---|---|---|---|---|
| R1 | R2 | H | Area mils$^2$ | Volume mils$^3$ | R1 | R2 | H | Area mm$^2$ | Volume nL |
| 1.44 | 0.67 | 2 | 14.21 | 7.30 | 36.6 | 17.0 | 50.8 | 0.0092 | 0.1197 |
| 1.93 | 1.25 | 2 | 21.10 | 16.13 | 49.0 | 31.8 | 50.8 | 0.0136 | 0.2643 |
| 2.56 | 1.61 | 2 | 29.01 | 27.79 | 65.0 | 40.9 | 50.8 | 0.0187 | 0.4553 |
| 3.11 | 2.24 | 2 | 36.66 | 45.36 | 79.0 | 56.9 | 50.8 | 0.0237 | 0.7433 |
| 3.27 | 2.56 | 2 | 38.87 | 53.65 | 83.1 | 65.0 | 50.8 | 0.0251 | 0.8792 |
| 3.43 | 1.85 | 5 | 86.98 | 112.75 | 87.1 | 47.0 | 127 | 0.0561 | 1.8476 |
| 5.28 | 3.35 | 5 | 145.31 | 297.35 | 134.1 | 85.1 | 127 | 0.0937 | 4.8726 |
| 5.94 | 4.01 | 5 | 167.53 | 393.66 | 150.9 | 101.9 | 127 | 0.1081 | 6.4509 |

FIG. 3 shows a cutaway side elevational view of each of the pore types conforming with the dimensions given above. The wafers were then cleaned with TEXWIPE™ iso-propyl a alcohol (IPA) cloths. This cleaning visibly reduced the residue left from the laser ablation. After the first cleaning process, the wafers were then cleaned using an oxygen plasma etch as detailed below.

The eight samples were suspended on a wire frame to expose both sides to the oxygen plasma etch. The etch was set at 150 watts, 100 millitorr of vacuum and an oxygen flow rate of 100 mls./min. To compensate for possible chamber/plasma irregularities, two five-minute etches were used with an 180° rotation between intervals. The cleaning method resulted in the entrance side of the wafer being free of residue. The exit side of the wafer had microscopic residue remaining.

After plasma cleaning the wafers were re-measured to see if the cleaning had changed their pore characteristics. The following table describes the dimensions of the various pores both before and after cleaning. The wafers were numbered in the following manner. A diamond scribe was used to "scratch" the number into the lower left corner of the exit side of the wafer.

Pore Diameters After Plasma Cleaning

|       | Material Code | Exit Dia. $\mu$ | Change in $\mu$ | Entrance Dia $\mu$ | Change in $\mu$ |
|-------|---------------|-----------------|------------------|--------------------|-----------------|
| Wafer #1: | 200VN | 18 | (+1) | 37 | (+0.5) |
| #2: | 200VN | 32 | (=) | 54 | (+5) |
| #3: | 200VN | 41 | (=) | 67 | (+2) |
| #4: | 200VN | 60 | (+3) | 80 | (+1) |
| #5: | 200VN | 68 | (+3) | 88 | (+5) |
| #6: | 500VN | 50 | (+3) | 92 | (+5) |
| #7: | 500VN | 86 | (+1) | 156 | (+22) |
| #8: | 500VN | 102 | (=) | 174 | (+23) |

Formation of Electrodes

Six of the eight sheets were then coated with 3000 Angstroms of a diamond-like carbon amorphous film via chemical vapor deposition (CVD) and then sputtered with 200 anstroms of chromium & 2000 angstroms of platinum. The intent was that the CVD and sputtered film would coat the interior surfaces of the pores so as to allow them to act as electrodes in the electrochemical reaction of the sensor.

Before the individual wafers were cut from the sheets they were first mounted to a sheet of 5 mil MYLAR™ to stiffen them & also provide a recess to keep the pore faces from contacting the surface on which it may be laying. The MYLAR™ was applied so over the exit side of the laser drilled so that the metalized (entrance) side of each button was left unobstrtucted. The MYLAR™ film was first punched with a 0.15" dia punch in the center location where each wafer would lie on the MYLAR™. The entire MYLAR™ was then adhered to the KAPTON™ film wafer using double sided tape, which had been applied to the MYLAR™ before punching. After this, the wafer "buttons" were then punched out using a 0.380" dia. punch.

Chemical Preparation

As discussed in detail below, the chemical preparation of the wafers was divided into three steps: first, for wafers utilizing a diffusion barrier, the pores were filled with a polymer solution, which, after drying, created a film that serves as a diffusion barrier. Second, the remaining pore volume was filed with an enzyme mixture. Third, after the curing of the enzyme solution and the attachment of a wire to the platinum surface of the film outside the region of the pores, the enzyme and entire backside of the sensor was covered with a protective film of silicone rubber to prevent the testing solution from flowing through the pore and contaminating the back side of the microfluidic device containing the wafer platform.

In those cases where a diffusion-controlling outer membrane was incorporated into the wafer, those membranes were made of polyvinyl alcohol (PVA). The films were made by filling the pore with the PVA solution (a 5% solution of 100% hydrolyzed PVA having an average molecular weight of 86,000) and removing the excess, allowing approximately one pore volume of solution to remain in the pore to evaporate. During evaporation the remaining solution was drawn to the narrow end of the pore due to capillary forces thereby creating a film at the small end of the pore. After drying, this film was cured to cross-link the PVA making it less apt to re-dissolve when exposed to potential solvents.

In those cases where a diffusion-controlling outer membrane was not incorporated, the enzyme solution was applied in a similar fashion (as with the PVA) except that excess solution was applied so that a thicker membrane of chemically cured enzyme material remained in the pore. The enzyme solution used in the pore sensors consisted of glucose oxidase (12.5 mg) in a solution (125 $\mu$l) of buffer salts (citrate-succinate buffer, pH 5.5). Glutaraldehyde (187.5 $\mu$l of 2.5% solution) was added to this mixture to induce chemical cross-linking of the oxidase protein.

Results

In general, all of the pore sensors evaluated which had the PVA outer diffusion membrane exhibited good sensitivity and linearity. The graph shown in FIG. 4 depicts the results for one such sensor.

The graph shown in FIG. 5 depicts the results obtained with a similar pore sensor configuration, except that it contained no outer membrane to act as a diffusion controlling layer. In this sensor the only obstacles to diffusion were the enzyme matrix itself & the geometry of the pore. Surprisingly, these appear to be enough to support a very good linear range. It is noted that the same enzyme medium deposited upon a flat electrode on a planar substrate would exhibit a very limited range of linearity, probably less that 10 mM.

Accordingly, having described the invention in detail, it will be apparent that modifications and variations are possible without departing from the scope of the invention defined in the appended claims.

What is claimed is:

1. A method of forming a platform for use in a microfluidic sensor comprising:

selecting a polymeric film;

laser drilling at least one frustoconical pore in said film such that said pore has a large diameter portion and a small diameter portion, said small diameter portion facing an analyte containing fluid when the microfluidic sensor is in use;

depositing a layer of metal suitable for use as an electrode over a wall of said pore; and depositing a membrane capable of detecting an analyte in said pore over said metal layer.

2. The method of claim 1 wherein said polymeric film is a polyimide.

3. The method of claim 2 wherein said polyimide is a self-bonding polyimide.

4. The method of claim 1 wherein said pore wall has a taper angle less than 15 degrees.

5. The method of claim 1 further comprising depositing a layer of amorphous carbon over said wall of said pore prior to depositing said layer of metal.

6. The method of claim 5 further comprising the step of, after depositing said layer of amorphous carbon, depositing an adhesion layer over said wall of said pore prior to depositing said layer of metal suitable for use as an electrode.

7. The method of claim 1 wherein said metal is platinum.

8. The method of claim 1 further comprising depositing a diffusion limiting layer in said small diameter portion of said pore.

9. The method of claim 8 wherein said diffusion limiting layer is polyvinyl alcohol.

10. The method of claim 1 further comprising forming a diffusion limiting layer in said pore at an exit end of said small diameter portion of said pore before depositing a membrane capable of detecting an analyte in said pore.

* * * * *

UNITED STATES PATENT AND TRADEMARK OFFICE
CERTIFICATE OF CORRECTION

PATENT NO. : 6,770,322 B1
DATED : August 3, 2004
INVENTOR(S) : Donald R. Moles

It is certified that error appears in the above-identified patent and that said Letters Patent is hereby corrected as shown below:

Title page,
Item [73], Assignee, after "Springs," change "CO" to -- OH --.

Signed and Sealed this

First Day of February, 2005

JON W. DUDAS
*Director of the United States Patent and Trademark Office*